United States Patent
Dugan et al.

(10) Patent No.: US 9,968,755 B2
(45) Date of Patent: *May 15, 2018

(54) PRESSURE RELIEF IN A RESPIRATORY ASSISTANCE SYSTEM

(71) Applicant: CAREFUSION 207, INC., San Diego, CA (US)

(72) Inventors: Greg J. Dugan, Corona, CA (US); Andre M. Rustad, Etiwanda, CA (US); Brian W. Pierro, Yorba Linda, CA (US)

(73) Assignee: CAREFUSION 207, INC., San Diego, CA (US)

( * ) Notice: Subject to any disclaimer, the term of this patent is extended or adjusted under 35 U.S.C. 154(b) by 163 days.

This patent is subject to a terminal disclaimer.

(21) Appl. No.: 14/838,089

(22) Filed: Aug. 27, 2015

(65) Prior Publication Data

US 2015/0367096 A1 Dec. 24, 2015

Related U.S. Application Data

(63) Continuation of application No. 13/359,773, filed on Jan. 27, 2012, now Pat. No. 9,149,598.

(Continued)

(51) Int. Cl.
*A61M 16/20* (2006.01)
*A61M 16/00* (2006.01)
(Continued)

(52) U.S. Cl.
CPC ...... *A61M 16/201* (2014.02); *A61M 16/0003* (2014.02); *A61M 16/0057* (2013.01);
(Continued)

(58) Field of Classification Search
CPC . A61G 10/023; A61M 16/00; A61M 16/0003; A61M 16/0051; A61M 16/0057;
(Continued)

(56) References Cited

U.S. PATENT DOCUMENTS 3,835,646 A 9/1974 Ranft et al.
3,933,171 A 1/1976 Hay
(Continued)

FOREIGN PATENT DOCUMENTS

AU 2009202427 1/2011
CN 101816815 A 9/2010
(Continued)

OTHER PUBLICATIONS

Japanese Office Action for Application No. 2013-551399, dated Oct. 20, 2015, 12 pages.
(Continued)

*Primary Examiner* — Annette Dixon
(74) *Attorney, Agent, or Firm* — McDermott Will & Emery LLP

(57) ABSTRACT

A pressure relief device comprising a valve configured to resiliently deform in response to a predetermined pressure; and a sound dampener configured to dampen a sound generated by the valve when the valve resiliently deforms in response to the predetermined pressure.

20 Claims, 8 Drawing Sheets

Related U.S. Application Data

(60) Provisional application No. 61/437,479, filed on Jan. 28, 2011.

(51) Int. Cl.
*A61M 16/06* (2006.01)
*A61M 16/08* (2006.01)

(52) U.S. Cl.
CPC .... *A61M 16/0666* (2013.01); *A61M 16/0875* (2013.01); *A61M 16/208* (2013.01); *A61M 16/209* (2014.02); *A61M 2205/3331* (2013.01); *A61M 2205/42* (2013.01)

(58) Field of Classification Search
CPC .......... A61M 16/0063; A61M 16/0666; A61M 16/0833; A61M 16/0875; A61M 16/1045; A61M 16/1055; A61M 16/107; A61M 16/16; A61M 16/20; A61M 16/201; A61M 16/202; A61M 16/206; A61M 16/208; A61M 16/209; A61M 2016/0027; A61M 2205/3331; A61M 2205/3358; A61M 2205/42; A61M 2230/432; F01N 3/22; F01N 3/227; F02B 61/045; F16K 11/10; F16K 17/082; F16K 17/085; F16K 41/10; F16N 39/00; G05D 16/02; G05D 16/0663; G05D 16/0669; Y10T 137/2574; Y10T 137/261; Y10T 137/2612; Y10T 137/2615; Y10T 137/263; Y10T 137/2693; Y10T 137/7757; Y10T 137/7793; Y10T 137/7794; Y10T 137/7812; Y10T 137/7821; Y10T 137/7832; Y10T 137/7879; Y10T 137/7904
USPC ............ 128/201.23, 202.22, 204.19, 205.24; 137/115.01, 115.14, 115.15, 115.21, 137/116.5, 119.08, 484.8, 505, 505.11, 137/505.29, 505.37, 506, 528, 843; 251/129.16, 335.3, 61.1, 77, 80
See application file for complete search history.

(56) References Cited

U.S. PATENT DOCUMENTS

| | | | |
|---|---|---|---|
| 3,934,413 A | 1/1976 | Beiswenger et al. | |
| 4,178,953 A | 12/1979 | White | |
| 4,190,045 A | 2/1980 | Bartels | |
| 4,259,951 A | 4/1981 | Chernack et al. | |
| 5,218,984 A | 6/1993 | Allen | |
| 5,586,569 A * | 12/1996 | Hanning ............ | G05D 16/0663 137/116.5 |
| 6,464,053 B1 | 10/2002 | Hoebrechts | |
| 6,804,656 B1 | 10/2004 | Rosenfeld et al. | |
| 7,207,945 B2 | 4/2007 | Bardy | |
| 7,520,277 B1 | 4/2009 | Grady | |
| 7,959,574 B2 | 6/2011 | Bardy | |
| 8,327,848 B2 | 12/2012 | Ho et al. | |
| 8,342,201 B2 * | 1/2013 | Nitta .................. | G05D 16/0669 137/505.11 |
| 8,343,233 B2 | 1/2013 | Perkins et al. | |
| 9,149,598 B2 * | 10/2015 | Dugan ................ | A61M 16/208 |
| 2004/0107965 A1 | 6/2004 | Hickle et al. | |
| 2006/0144396 A1 | 7/2006 | DeVries et al. | |
| 2007/0083677 A1 | 4/2007 | Cecka et al. | |
| 2008/0078395 A1 | 4/2008 | Ho et al. | |
| 2011/0022182 A1 | 1/2011 | Perkins et al. | |

FOREIGN PATENT DOCUMENTS

| | | |
|---|---|---|
| EP | 0911054 | 4/1999 |
| JP | H07275361 A | 10/1995 |
| JP | 2010504842 A | 2/2010 |
| RU | 2154503 C2 | 8/2000 |
| RU | 2215547 C1 | 11/2003 |

OTHER PUBLICATIONS

Mexican First Office Action for Application No. MX/a/2013/008641, dated Aug. 7, 2015, 4 pages.
Chinese Second Office Action for Application No. 201280006459.1, dated Dec. 9, 2015, 18 pages.
Russian Office Action for Application No. 2013134487, dated Dec. 10, 2015, 9 pages.
Mexican Notice of Allowance for Application No. MX/a/2013/008641, dated Nov. 25, 2015, 4 pages.
European Office Action for Application No. 12739007.8, dated Mar. 4, 2016, 4 pages.
Australian Notice of Acceptance for Application No. 2012211062, dated Mar. 18, 2016, 2 pages.
Russian Office Action for Application No. 2013134487, dated Mar. 22, 2016, 7 pages excluding translation.
Chinese Third Office for Application No. 201280006459.1, dated Jun. 3, 2016, 7 pages excluding translation.
Japanese Office Action for Application No. 2013-551399, dated Jun. 28, 2016, 4 pages excluding translation.
Australian Examination Report No. 1 for Application No. 2012211062, dated Jul. 1, 2015, 3 pages.
Chinese First Office Action for Application No. 201280006459.1, dated Mar. 23, 2015, 12 pages.
Extended European Search Report for Application No. 12739007.8, dated Jun. 29, 2015, 7 pages.
International Search Report and Written Opinion for Application No. PCT/US2012/023038, dated Aug. 22, 2012, 8 pages.
Canadian Office Action for Application No. 2825832, dated Nov. 7, 2017, 3 pages.
Japanese Office Action for Application No. 2016-211604, dated Sep. 5, 2017, 4 pages excluding translation.

* cited by examiner

430B

PRESSURE RELIEF IN A RESPIRATORY ASSISTANCE SYSTEM

CROSS-REFERENCE TO RELATED APPLICATIONS

This application is a continuation of U.S. patent application Ser. No. 13/359,773, filed Jan. 27, 2012, entitled "PRESSURE RELIEF IN A RESPIRATORY ASSISTANCE SYSTEM," that claims priority to and benefit of U.S. Provisional Patent Application Ser. No. 61/437,479, filed Jan. 28, 2011, entitled "PRESSURE-LIMITED VARIABLE-FLOW NASAL CPAP SYSTEM," the disclosure of which is incorporated herein by reference in its entirety.

BACKGROUND

Breathing assistance systems are utilized to treat patients experiencing respiratory difficulties and/or insufficiencies. In some instances, the gas source for such systems may generate elevated pressures above a desired pressure threshold. As a result, the elevated pressures can result in barotrauma to the patient.

Moreover, some devices within the breathing assistance systems can generate loud sounds during operation. As a result, the loud sounds may irritate or harm the patients (e.g., neonates).

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
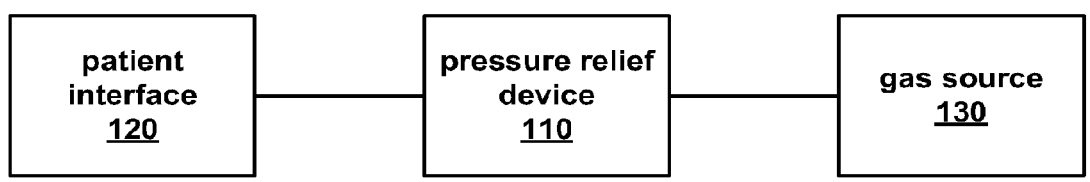
FIG. 1 illustrates an embodiment of a respiratory assistance system.

FIG. 1 depicts an embodiment of respiratory assistance system 100. System 100 can be any respiratory system that generates a gas source for respiratory assistance. Such systems (e.g., invasive or non-invasive) can be, but are not limited to, a ventilator system, a continuous positive airway pressure (CPAP) system, a nasal CPAP (nCPAP) system, a pressure limited variable flow nCPAP system, etc.

System 100 includes pressure relief device 110, patient interface 120 and gas source 130. Relief device 110, patient interface 120 and gas source 130 are fluidly connected with one another via tubing.

Patient interface 120 can be, but is not limited to, a single limb interface, a double limb interface, a CPAP generator, etc.

Gas source 130 can be, but is not limited to, a flow driver for a CPAP system, a ventilator for a ventilator system, etc.

It should be appreciated that the flow driver provides a CPAP generator with a flow of gas. The CPAP generator receives the flow of gas (e.g., air and/or oxygen) and subsequently generates a CPAP to be delivered to the patient. The CPAP can be generated by various physical features within the generator, such as but not limited to contours, jets, etc. Typically, flow drivers in a CPAP system operate at higher pressures than the operating pressures of a ventilator system.

In general, in a ventilator system, the requisite air flow and pressure is mechanically generated at the ventilator. The requisite airflow is then delivered to the patient via a patient interface.

Pressure relief device 110 is any pressure relief device that relieves pressure in system 100. In particular, pressure relief device 110 ensures that a pressure in system 100 does not exceed a predetermined pressure. For example; a patient receives a first pressure of gas at patient interface 120 for respiratory assistance. Gas source 130 generates a second pressure of gas which is greater than the first pressure. If the patient receives the second pressure of gas, then barotrauma may result. However, pressure relief device 110, in response to the second pressure, relieves or vents gas from system 100 such that the patient does not receive the second pressure. In one embodiment, pressure relief device 110 vents gas from system 100 such that the pressure in system 100 is the prescribed pressure for the patient.

In one embodiment, pressure relief device 110 disposed in the source gas line (as depicted in FIG. 1). In another embodiment, pressure relief device 110 is disposed proximate, or integral with patient interface 120. In a further embodiment, pressure relief device 110 is disposed proximate, or integral with gas source 130.

Figure 3:
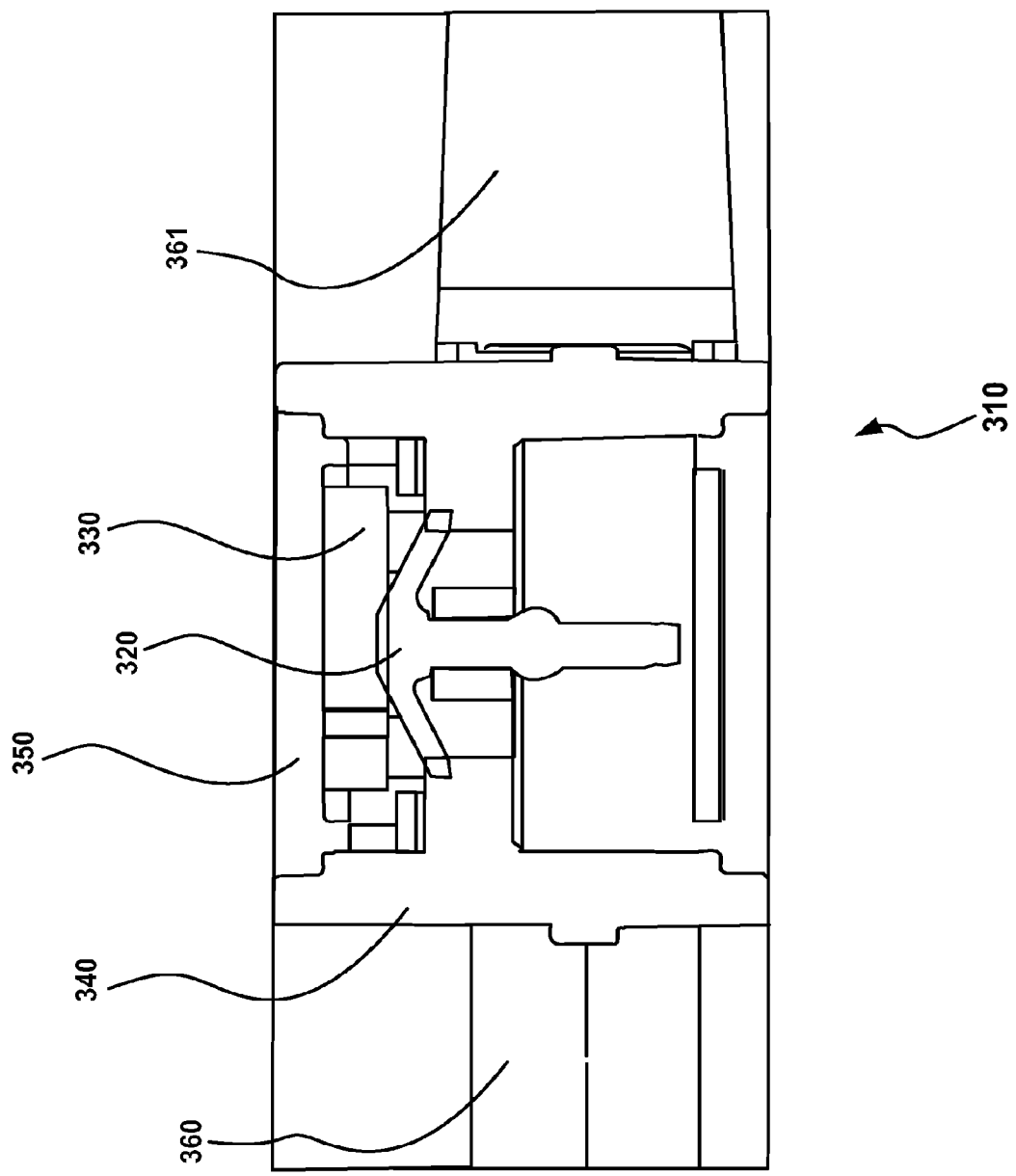
FIG. 3 illustrates an embodiment of a pressure relief device.

In one embodiment, pressure relief device 110 is an umbrella valve device, such as pressure relief device 310, as depicted in FIG. 3. A detailed description of pressure relief device 310 is provided below.

Figure 2:
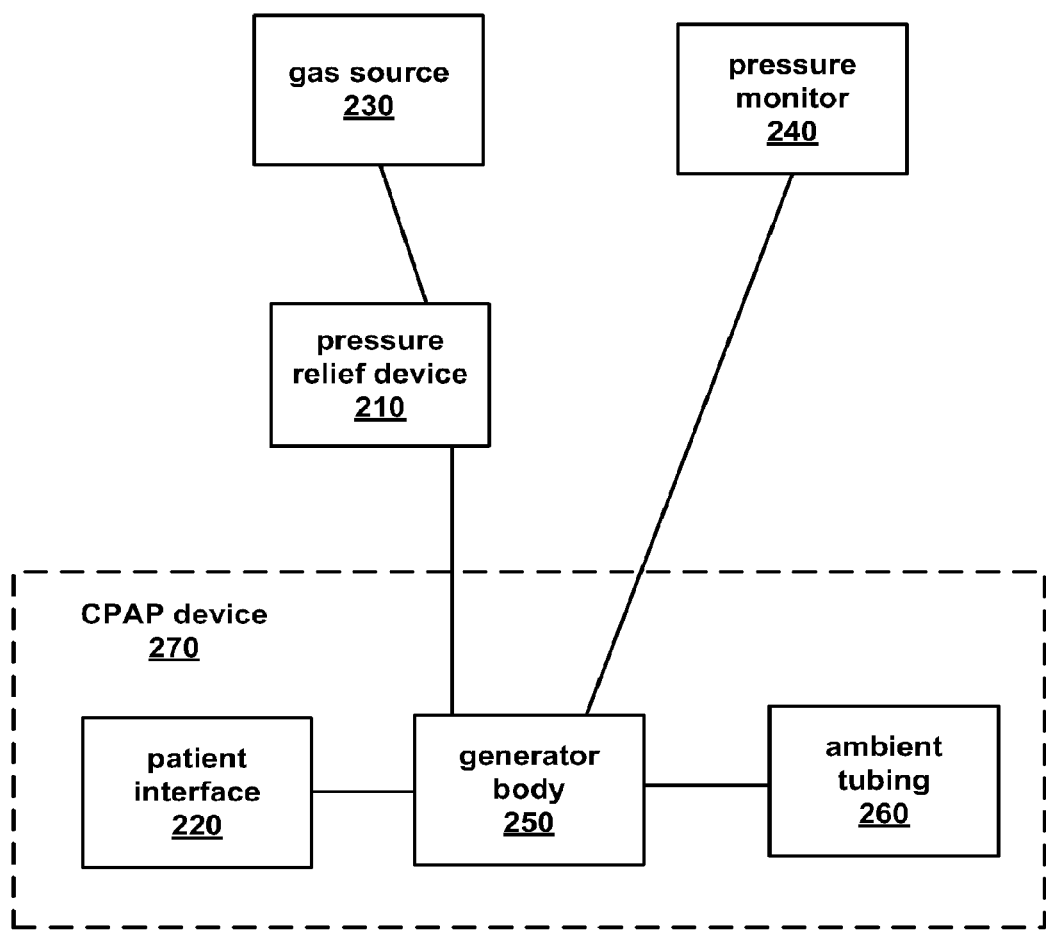
FIG. 2 illustrates an embodiment of a respiratory assistance system.

FIG. 2 depicts an embodiment of respiratory assistance system 200. In particular, system 200 is a CPAP system. In various embodiments; the CPAP system is pressure-limited variable-flow CPAP (or nCPAP) system.

Conventional variable flow CPAP systems typically utilize a substantially higher drive pressure, for example, in excess of 200 cmH2O, to create CPAP pressures of up to 20 cmH2O. In contrast, system 200 (e.g.; a pressure-limited CPAP system) utilizes lower drive pressure, for example 60 cmH2O, to create CPAP pressures up to 20 cmH2O.

A "variable flow" system, in general, allows for some degree of control of gas flow and/or oxygen concentration of the CPAP system. In contrast, a fixed (or non-variable flow) CPAP system does not allow for control of gas flow and/or oxygen concentration.

System 200 includes a gas source 230 (e.g., a flow driver) that provides gas to CPAP device 270. In particular, generator body 250 receives the gas from gas source 230. Generator body 250 receives the flow of gas (e.g., air and/or oxygen) and subsequently generates a CPAP to be delivered to the patient. The CPAP can be generated by various physical features within the generator body 250, such as but not limited to contours, jets, etc.

The CPAP is received by the patient via patient interface 220. When the patient exhales, the exhalation is passes through patient interface 220, generator body 250 and exits system 200 at ambient tubing 260.

In one embodiment, system 200 includes pressure monitor 240 configured to monitor pressure in system 200.

It should be appreciated that variable-flow nCPAP devices (e.g., Infant Flow nCPAP, Airlife nCPAP) are traditionally operated by connecting to a flow-driving device. These devices operate at drive pressures significantly higher than devices used for ventilation purposes. In order to utilize a variable-flow device on a ventilator platform, the drive pressure must be reduced significantly.

Conventional CPAP flow-driving devices are compatible with low-drive pressure nCPAP systems, such as CPAP device 270 when the flow driver is functional and monitoring the patient pressure. However, flow drivers that have the ability to administer flow without monitoring (e.g., Infant Flow SiPAP, P-Driver) rely on drive pressure to trigger a relief mechanism, by the flow-driving device when the monitoring is turned off. A typical relief mechanism is a spring loaded mechanical relief valve which operates at pressures above 200 cmH2O, integrated within the CPAP driver, and suitable for multi-patient use.

In contrast, pressure relief device 210 is a disposable device. In one embodiment, pressure relief device operates at pressures above 60 cmH2O. In another embodiment, pressure relief device 210 is reusable for single patient use.

When using a variable-flow CPAP system, such as system 200, which requires less drive pressure to obtain the same patient pressure, increasing the drive pressure to levels deemed acceptable for older, high-drive pressure variable-flow systems would result in much higher pressure seen by the patient when no monitoring occurs. This could result in barotrauma to the patient. Incorporating a pressure-relief mechanism (e.g.; pressure relief device 210) would ensure that this scenario of high patient pressures as a result of unmonitored high drive pressures on a flow driver device would not cause unwanted high pressures to be seen by the patient.

Therefore, incorporating a pressure-relief system (e.g., pressure relief device 210) that vents at a desired pressure (can be related to both the drive or patient pressure) allows for the variable-flow nCPAP device (e.g., system 200) to be used safely on both an old flow-driving device, as well as, have low-enough drive pressure for compatibility with ventilator platforms.

In one embodiment, pressure relief device 210 is disposed in the source gas line (as depicted in FIG. 2). In another embodiment, pressure relief device 210 is disposed proximate, or integral with CPAP device 270 and in particular, with generator body 250. In a further embodiment, pressure relief device 210 is disposed proximate, or integral with gas source 230.

FIG. 3 depicts an embodiment of a pressure relief device 310. Pressure relief device 310 is an umbrella relief device. In particular, pressure relief device 310 includes umbrella valve 320 and sound dampener 330 disposed in housing 340. For example, sound dampener 330 is disposed between lid 350 and umbrella valve 320.

Umbrella valve 320 is configured to unseal with housing 340 at a predetermined pressure. For example, umbrella valve 320 is sealed with the interior of housing 340 at a first pressure, such that airflow passes through tubes 361 and 360. For instance, at the first pressure, umbrella valve 320 is sealed such that air flow is effectively delivered from a gas source to a patient interface. It should be appreciated that air flow can flow in the direction of tube 360 to tube 361 or in the direction from tube 361 to tube 360.

However, if pressure in the system increases to a predetermined pressure (higher than the first pressure), then umbrella valve resiliently deforms to allow gas flow to pass out of a plurality of vents in housing 340 to relieve the pressure in the system. The predetermined pressure is also known as the cracking, opening or relieving pressure.

Umbrella valve 320 generates a high noise level (e.g., 80-85 db) when it deforms in response to the predetermined pressure. This high noise level can irritate patients, especially those with sensitive hearing, such as neonates. In some instances, the generated high noise level may harm the hearing of the patient.

However, sound dampener 330 dampens the noise level generated by umbrella valve 320. For example, as umbrella valve 320 deforms, it physically contacts sound dampener 330. In one embodiment, when the relief valve is activated, the sound generated by umbrella valve 320 is reduced to 50 db or less.

In one embodiment, the sound is reduced at a prescribed range of around ≤35 liters per minute (LPM) drive flow. In another embodiment, the sound is reduced at a prescribed range of around ≤20 LPM drive flow.

Sound dampener 330 can be any material that facilitates in dampening the sound generated by umbrella valve 320. In one embodiment, sound dampener 330 is polyurethane foam. In various embodiments, sound dampener 330 can be, but is not limited to, felt, cloth, any perforated material, etc.

Sound dampener 330 can be die cut or laser cut. It should be appreciated that the edges of sound dampener are straight. In other words, the edges of the sound damper have no or very limited roundness or taper.

Sound dampener 330 also reduces the standard deviation the cracking pressure of umbrella valve 320. For example, umbrella valve 320 deforms or cracks between 50 and 70 cc $H_2O$, when sound dampener is not utilized. However, when sound dampener 330 is utilized, the standard deviation of the cracking pressure is narrowed such that the umbrella valve 320 consistently cracks on or around 60 cc$H_2O$.

Figure 4A:
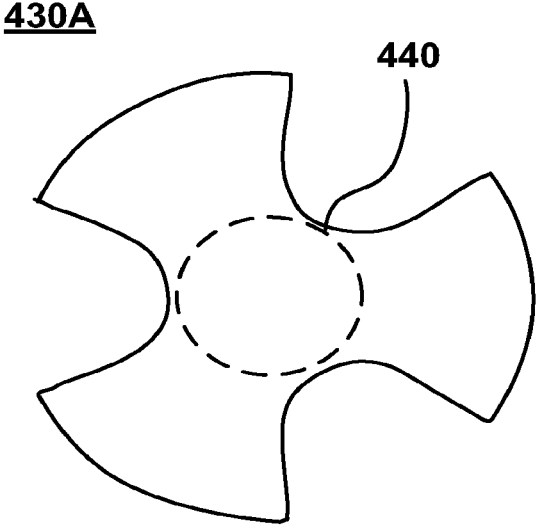
FIGS. 4A-E illustrates embodiments of a sound dampener.

FIGS. 4A-E depicts embodiments of sound dampeners 430A-E, respectively. FIG. 4A depicts sound dampener 430A with a pin wheel shape. In one embodiment, sound dampener 430A includes centering feature 440 configured to facilitate in the centering of sound dampener 430A within housing 340. Centering feature 440 can be any shape that is compatible for centering. For example, centering feature 440 can be, but is not limited, to a hole, void, indentation, bulge, ridge, ring, peg(s) or post(s), etc. In another embodiment, centering feature 440 corresponds with a centering feature on lid 350.

Figure 4B:
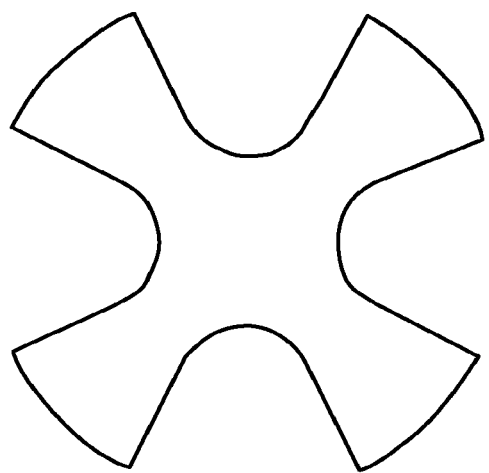
Figure 4C:
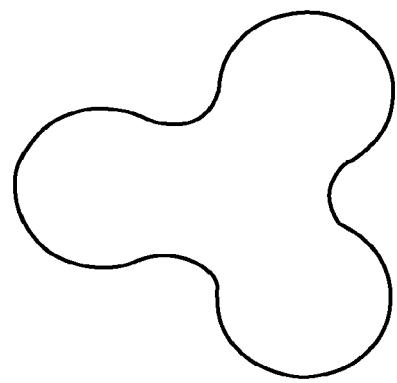
Figure 4D:
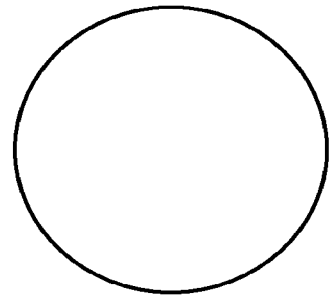
Figure 4E:
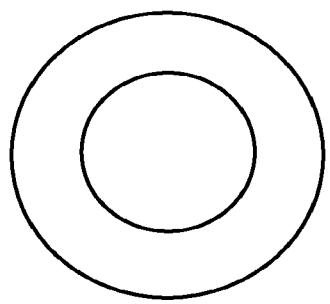

FIG. 4B depicts sound dampener 430B with a pin wheel shape. FIG. 4C depicts sound dampener 430C with a clover leaf shape. FIG. 4D depicts sound dampener 430D with a disk shape. FIG. 4E depicts sound dampener 430E with a ring shape. It should be appreciated that the depicted shapes are not limiting or exhaustive. As such, the sound dampener can be any shape that is able to dampen sound of umbrella valve 320.

Various embodiments are thus described. While particular embodiments have been described, it should be appreciated that the embodiments should not be construed as limited by such description, but rather construed according to the following claims.

The invention claimed is:

1. A method of controlling fluid pressure through a pressure relief device, the method comprising:
   connecting the pressure relief device to a respiratory assistance system, the pressure relief device comprising a housing having a vent, a first tube, and a second tube fluidly coupled within the housing, the vent defining a passage from within the housing to an ambient environment;
   retaining a valve within the housing to obstruct the vent, the valve being retained between the vent, the first tube, and the second tube; and
   resiliently deforming said valve, in response to a predetermined pressure in the respiratory assistance system, to (i) fluidly couple the vent, the first tube, and the second tube, and (ii) contact a sound dampener to dampen a sound generated by said valve when said valve resiliently deforms.

2. The method of claim 1, further comprising connecting the pressure relief device between a gas source and a patient interface.

3. The method of claim 1, further comprising sealing the valve with the housing at a first pressure so that a flow passes through the first tube and the second tube.

4. The method of claim 1, wherein said valve is an umbrella valve.

5. The method of claim 1, wherein the predetermined pressure is greater than the first pressure.

6. The method of claim 1, further comprising providing a lid coupled to the housing, wherein said sound dampener is disposed between said lid and said valve.

7. The method of claim 1, further comprising centering said sound dampener within said housing with a centering feature of said sound dampener.

8. The method of claim 7, further comprising centering said sound dampener with a corresponding centering feature of a lid coupled to the housing.

9. The method of claim 1, wherein a shape of said sound dampener is selected from a group consisting of: a disk shape, a ring shape, a clover-like shape, and a pinwheel-like shape.

10. The method of claim 1, wherein said respiratory assistance system is a continuous positive airway pressure (CPAP) system.

11. The method of claim 1, wherein said respiratory assistance system is a nasal continuous positive airway pressure (nCPAP) system.

12. The method of claim 1, wherein said patient interface comprises a CPAP generator.

13. The method of claim 1, wherein said patient interface comprises an nCPAP generator.

14. The method of claim 1, wherein said first tube and said second tube are collinear.

15. The method of claim 1, wherein said first tube and said second tube are fluidly coupled when said valve is not deformed.

16. A method of controlling fluid pressure in a variable-flow continuous positive airway pressure (CPAP) system, the method comprising:
    connecting a pressure relief device between a flow driver and a CPAP generator, the pressure relief device comprising a housing having a vent, a first tube, and a second tube fluidly coupled within the housing, the vent defining a passage from within the housing to an ambient environment;
    retaining a valve within the housing to obstruct the vent, the valve being retained between the vent, the first tube, and the second tube; and
    resiliently deforming said valve, in response to a predetermined pressure in the variable-flow CPAP system, to (i) fluidly couple the vent, the first tube, and the second tube, and (ii) contact a sound dampener to dampen a sound generated by said valve when said valve resiliently deforms.

17. The method of claim 16, further comprising sealing the valve with the housing at a first pressure so that a flow passes through the first tube and the second tube.

18. The method of claim 16, wherein said valve is an umbrella valve.

19. The method of claim 16, wherein the predetermined pressure is greater than the first pressure.

20. The method of claim 16, wherein a shape of said sound dampener is selected from a group consisting of: a disk shape, a ring shape, a clover-like shape, and a pinwheel-like shape.

* * * * *